(12) United States Patent
Liu (10) Patent No.: US 10,842,397 B2
(45) Date of Patent: Nov. 24, 2020

(54) FLEXIBLE SENSOR AND APPLICATION THEREOF

(71) Applicant: SHENZHEN RUIHU TECHNOLOGY CO., LTD, Guangdong (CN)

(72) Inventor: Jianhui Liu, Guangdong (CN)

(73) Assignee: SHENZHEN RUIHU TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 16/340,494

(22) PCT Filed: Dec. 6, 2017

(86) PCT No.: PCT/CN2017/114852
§ 371 (c)(1),
(2) Date: Apr. 9, 2019

(87) PCT Pub. No.: WO2018/064989
PCT Pub. Date: Apr. 12, 2018

(65) Prior Publication Data
US 2020/0046236 A1    Feb. 13, 2020

(30) Foreign Application Priority Data

Oct. 9, 2016    (CN) .................... 2016 2 1106670 U
Dec. 6, 2016    (CN) .......................... 2016 1 1112677

(51) Int. Cl.
*G01L 1/00*    (2006.01)
*A61B 5/024*    (2006.01)
(Continued)

(52) U.S. Cl.
CPC ........ *A61B 5/02444* (2013.01); *A61B 5/0816* (2013.01); *G01L 1/18* (2013.01); *H05K 1/028* (2013.01); *H05K 1/0393* (2013.01)

(58) Field of Classification Search
CPC .. A61B 5/02444; A61B 5/0816; H05K 1/028; H05K 1/0393; G01L 1/18
(Continued)

(56) References Cited

U.S. PATENT DOCUMENTS 6,504,531 B1 * 1/2003 Sandbach ............... G06F 3/045
178/18.05
8,253,696 B2 * 8/2012 Antaki .................. G06K 9/0002
178/18.06
(Continued)

FOREIGN PATENT DOCUMENTS

CN    104880266 A    9/2015
CN    105115414 A    12/2015
(Continued)

OTHER PUBLICATIONS

International Search Report PCT/CN2017/114852, prepared by Intellectual Property Office of the P.R. China, dated Feb. 24, 2018, 3 pages.
(Continued)

*Primary Examiner* — Max H Noori
(74) *Attorney, Agent, or Firm* — Brooks Kushman P.C.

(57) ABSTRACT

A flexible sensor used for touch detection and an application thereof. The flexible sensor having a flexible substrate, at least two conductive layers and a plurality of electrodes, the conductive layers respectively covering two surfaces of the flexible substrate, the electrodes being arranged at two ends of the conductive layers, the conductive layers having a matrix and first conductive particles dispersed within the matrix. The sensor has stable output characteristics and good consistency between individuals, is easy to install, low-cost and highly sensitive, and can replace PVDF piezoelectric thin film sensors for monitoring human heartbeat and breathing state data.

13 Claims, 5 Drawing Sheets

(51) Int. Cl.
*A61B 5/08* (2006.01)
*G01L 1/18* (2006.01)
*H05K 1/02* (2006.01)
*H05K 1/03* (2006.01)

(58) Field of Classification Search
USPC .................................................. 73/862.625
See application file for complete search history.

(56) References Cited

U.S. PATENT DOCUMENTS

| | | | |
|---|---|---|---|
| 10,379,654 B2* | 8/2019 | Li | G01L 1/18 |
| 2011/0307214 A1* | 12/2011 | Saitou | G01B 7/16 |
| | | | 702/155 |
| 2013/0320467 A1* | 12/2013 | Buchanan | G06F 3/044 |
| | | | 257/419 |
| 2015/0323302 A1 | 11/2015 | Chuang et al. | |

FOREIGN PATENT DOCUMENTS

| | | |
|---|---|---|
| CN | 204861657 U | 12/2015 |
| CN | 105783697 A | 7/2016 |
| CN | 205593690 U | 9/2016 |
| CN | 106546162 A | 3/2017 |

OTHER PUBLICATIONS

Liu Xu et al., Preparation Solutions of Flexible PVDF Piezoelectric Film Sensor, published in the Instrument Technique and Sensor (Period 1, 2016), 9 pages including translation.

* cited by examiner

FLEXIBLE SENSOR AND APPLICATION THEREOF

CROSS-REFERENCE TO RELATED APPLICATION

This application is the U.S. national phase of PCT Application No. PCT/CN2017/114852 filed on Dec. 6, 2017, which claims priority to CN Patent Application No. 201611112677.X filed on Dec. 6, 2016, and CN Patent Application No. 201621106670.2 filed on Oct. 9, 2016, the disclosures of which are incorporated in their entirety by reference herein.

FIELD

Embodiments of the present disclosure generally relate to flexible sensors, and more particularly relate to a flexible sensor for sensing a strain, and an application thereof.

BACKGROUND

Conventional silicon-based sensors can hardly be adapted to a complex curved surface due to their characteristics such as fragility and incapability of enduring a relatively large deformation, rendering their applications restricted. PVDF (polyvinylidene fluoride), as the most idealized sensing material, have properties such as low charge response, ease of use, good pliability, and high sensitivity. Sensors fabricated with a PVDF piezoelectric film have extensive applications. The sensors fabricated with the PVDF film are far superior to those conventional silicon-based sensors. The soft and light PVDF film, which is a smart flexible sensing material, resembles much human skin. Flexible PVDF sensors fabricated using a flexible electronic technology have a good pliability and impact-resistance such that they may be adapted to more complex surfaces, thereby expanding their applications. Such new-model flexible PVDF sensors may be sufficiently attached to a human body for monitoring health conditions. *Preparation Solutions of Flexible PVDF Piezoelectric Film Sensor*, LIU Xu, et al., published in the Instrument Technique and Sensor (Period 1, 2016), discloses a PVDF piezoelectric film sensor structure with a flexible substrate, where a PVDF piezoelectric film with good properties is fabricated using PVDF powder, and a solution of fabricating a flexible PVDF film sensor is proposed. The structure of the PVDF piezoelectric film sensor comprises, in sequence from bottom to top, a PDMS layer, a bottom electrode, a PVDF film, a top electrode, and an epoxy adhesive. Laboratory fabrication of the sensor includes the following main processing steps: depositing a silicon dioxide layer; preparing a PDMS layer; metal sputtering to form a lower electrode layer; etching a bottom electrode layer; etching a sacrificial layer; device transferring; wire bonding; and surface reinforcing. However, that solution is complex in processing, difficult in wiring, and costly in manufacturing.

SUMMARY

A technical problem to be solved by the present disclosure is to provide a flexible sensor for sensing a strain. The flexible sensor for sensing a strain offers a simple processing, an ease of wiring, and a low manufacturing cost, which may replace a PVDF piezoelectric film sensor to monitor data about human body health conditions.

To solve the technical problem above, a flexible sensor for sensing a strain is provided, comprising: a strain film and a signal amplifying circuit, wherein the strain film includes a flexible substrate, a plurality of electrically conductive layers in parallel, and a plurality of electrodes, the electrodes including a power input end, an anode output end, and a cathode output end; the electrically conductive layers, which cover upper and lower surfaces of the flexible substrate, respectively, include a matrix and first electrically conductive particles which are dispersed in the matrix; and two ends of the respective electrically conductive layers are electrically connected to corresponding electrodes.

In the flexible sensor for sensing a strain, the electrically conductive layers include second electrically conductive particles, wherein the first electrically conductive particles are carbon powder or metal powder, the second electrically conductive particles are carbon fibers, nanometer carbon tubes or graphene, and two ends of the second electrically conductive particles face two electrodes, respectively.

In the flexible sensor for sensing a strain, the matrix is a polymer.

In the flexible sensor for sensing a strain, the strain film includes two elastic layers which cover outer surfaces of the electrically conductive layers.

In the flexible sensor for sensing a strain, the strain film includes 4 electrically conductive layers, the 4 electrically conductive layers being connected to form a Wheatstone bridge, wherein two opposite bridge arms of the Wheatstone bridge are disposed at a top face of the flexible substrate, and the other two opposite bridge arms are disposed at a bottom face of the flexible substrate.

In the flexible sensor for sensing a strain, the flexible substrate includes an upper substrate and a lower substrate which are folded together; two opposite bridge arms of the Wheatstone bridge cover an upper surface of the upper substrate, and the other two opposite bridge arms cover a lower surface of the lower substrate.

In the flexible sensor for sensing a strain, the signal amplifying circuit includes a differential capacitor, two negative feedback amplifying circuits and two low-pass filter circuits; the anode output end of the strain film is connected to a first negative feedback amplifying circuit via the differential capacitor, and the first negative feedback amplifying circuit is connected to a second negative feedback amplifying circuit via a first low-pass filter circuit; and the second negative feedback amplifying circuit gives an output via a second low-pass filter circuit.

In the flexible sensor for sensing a strain, the negative feedback amplifying circuit includes an operational amplifier and a negative feedback resistor, the negative feedback resistor being connected to an output end and an inverting input end of the operational amplifier; the first low-pass filter circuit includes a first filter resistor and a first filter capacitor, and the second low-pass filter circuit includes a second filter resistor and a second filter capacitor; the anode output end of the strain film is connected to the inverting input end of the operational amplifier of the first negative feedback amplifying circuit via the differential capacitor, and an output end of the operational amplifier of the first negative feedback amplifying circuit is connected to the inverting input end of the operational amplifier of the second negative feedback amplifying circuit via the first filter resistor through the negative input resistor; the output end of the operational amplifier of the second negative feedback amplifying circuit gives an output via the second filter resistor; a first end of the first filter capacitor is connected to a connection point between the first filter resistor and the negative input resistor, and a second end thereof is earthed; a first end of the second filter capacitor is connected to an output end of the second filter resistor, and a second end thereof is earthed; a non-inverting input end of the operational amplifier of the first negative feedback amplifying circuit and a non-inverting input end of the operational amplifier of the second negative feedback amplifying circuit are connected to the cathode output end of the strain film.

The flexible sensor for sensing a strain is applied to sense heartbeat or breathing of a human body.

The present disclosure has a simple structure, a simple processing technique, an ease of wiring, a low cost, and a high sensitivity, which may replace a conventional PVDF piezoelectric film sensor to monitor data about heartbeat or breathing status of a human body.

DETAILED DESCRIPTION OF EMBODIMENTS

Hereinafter, the present disclosure will be described in further detail through preferred embodiments with reference to the accompanying drawings.

Embodiment 1

The present disclosure provides a flexible sensor, which, more specifically, may be an electronic skin for touch sensing.

The structure of a strain film of the flexible sensor, as shown in FIGS. 1~4, comprises a flexible substrate (film) 1, two electrically conductive layers 2, two rubber elastic layers 3, and four electrodes 5. The four electrodes 5 include a power positive input end, a power negative end, an anode output end, and a cathode input end.

The two electrically conductive layers 2 cover upper and lower surfaces of the flexible substrate 1, respectively, and the rubber elastic layers 3 cover outside of the electrically conductive layers 2. The electrodes 5 are arranged at two ends of the electrically conductive layers 2. The electrically conductive layers 2 include a matrix 201, first electrically conductive particles (not shown) and second electrically conductive parties 202, the first electrically conductive particles and the second electrically conductive parties 202 being dispersed in the matrix 201, and two ends of the second electrically conductive particles 202 face the electrodes 5 at the two ends of the electrically conductive layers 2, respectively.

Particularly, the first electrically conductive particles are for example carbon powder or metal powder, and the second electrically conductive particles 202 may be carbon fibers, nanometer carbon tubes, or graphene. The matrix 201 is a polymer, wherein the polymer may be selected from the group consisting of epoxy resin, polyurethane or acrylic resin. The elastic layers 3 are rubber layers which cover outer surfaces of the electrically conductive layers 2.

The flexible substrate is made of, for example, polyethylene terephthalate PET or polyimide PI. The electrically conductive layers 2 on two faces of the flexible substrate 1 serve as a sensing material, such that when the strain film is stressed, the film will be flexed, presenting different impedances. By sensing variation of the impedance of the electrically conductive layers 2, the present disclosure may sense whether a deformation occurs.

Embodiment 2

Figure 1:
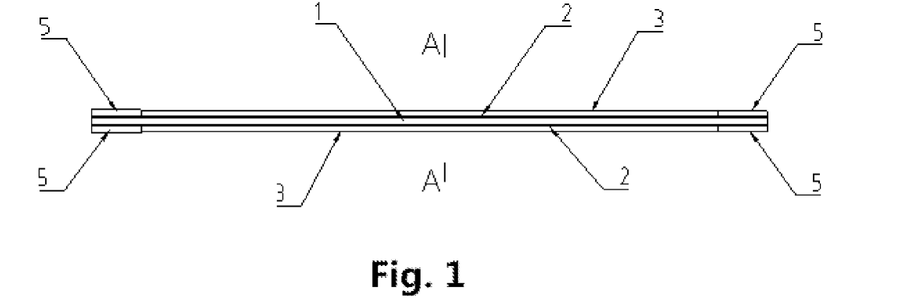
FIG. 1 is a front view of a strain film according to embodiment 1 of the present disclosure.
Figure 2:
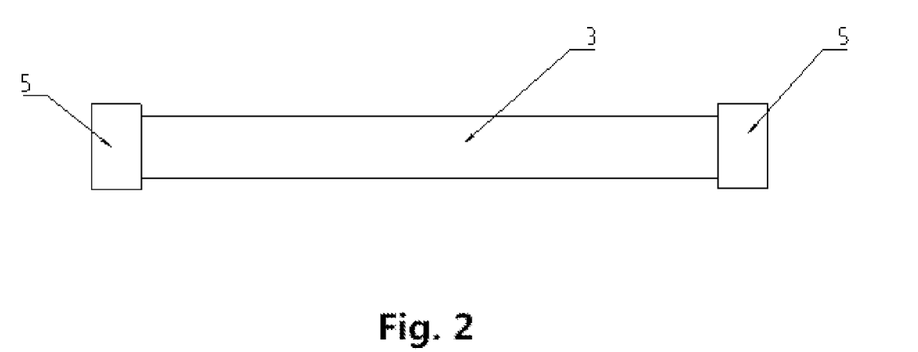
FIG. 2 is a top view of the strain film according to embodiment 1 of the present disclosure.
Figure 3:
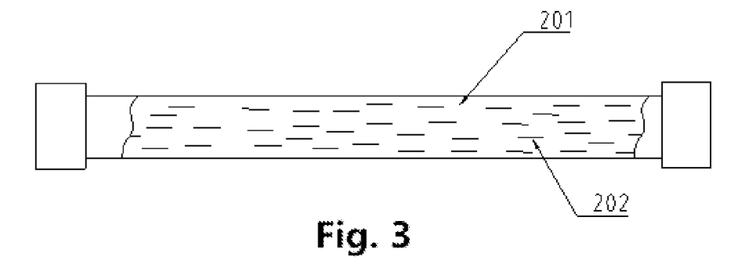
FIG. 3 is a top view of the strain film according to embodiment 1 of the present disclosure, where electrically conductive layers are shown.
Figure 4:
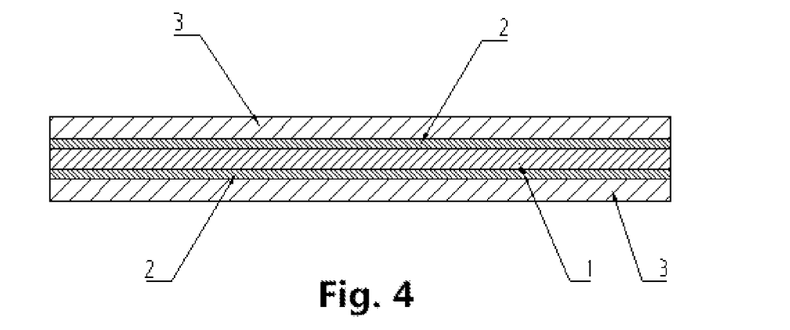
FIG. 4 is an A-A sectional view of FIG. 1.
Figure 5:
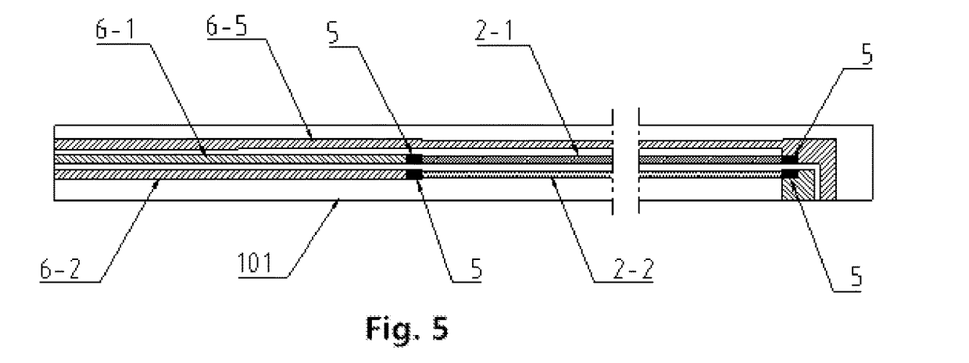
FIG. 5 is a front view of a strain film according to embodiment 2 of the present disclosure.
Figure 6:
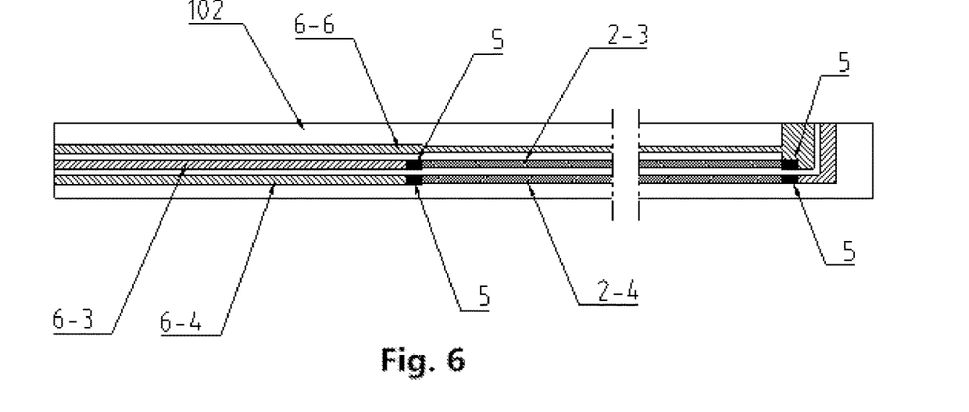
FIG. 6 is a bottom view of the strain film according to embodiment 2 of the present disclosure.
Figure 7:
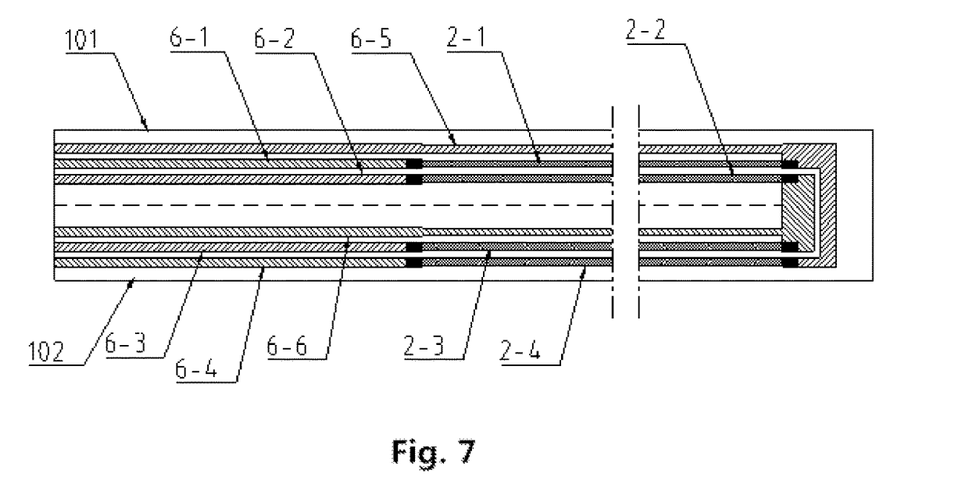
FIG. 7 is a structural view of the strain film in an unfolded state according to embodiment 1 of the present disclosure.

Another embodiment of a flexible sensor or electronic skin is provided, as shown in FIGS. 5~7. Different from Embodiment 1, the flexible sensor or electronic skin in Embodiment 2 comprises six leads and four electrically conductive layers 2, wherein the flexible substrate 1 includes an upper substrate 101 and a lower substrate 102 which are bonded together after being folded. Particularly, the upper substrate 101 and the lower substrate 102 are integrally bonded for example after folding a same block of flexible substrate material; the six leads and the four electrically conductive layers 2 are all printed on the upper surface of the flexible substrate material. In FIG. 7, the line 30 is a line for folding and clipping.

The four electrically conductive layers 2 are connected into a Wheatstone bridge; after the flexible substrate material is folded, two opposite bridge arms of the Wheatstone bridge, i.e., electrically conductive layer 2-1 and electrically conductive layer 2-2, cover an upper surface of the upper substrate 101, and the other two opposite bridge arms of the Wheatstone bridge, i.e., electrically conductive layer 2-3 and electrically conductive layer 2-4, cover a lower surface of the lower substrate 102.

The electrically conductive layer 2-1 is disposed over the electrically conductive layer 2-4; the electrode 5 at the right end of the electrically conductive layer 2-1 is electrically connected to the electrode 5 at the right end of the electrically conductive layer 2-4. The electrode 5 at the right end of the electrically conductive layer 2-2 is electrically connected to the electrode 5 at the right end of the electrically conductive layer 2-3.

The leads are, for example, silver paste wired, covering two surfaces of the folded flexible substrate 1; the right end of the lead 6-1 is connected to the electrode 5 at the left end of the electrically conductive layer 2-1, the right end of the lead 6-2 is connected to the electrode 5 at the left end of the electrically conductive layer 2-2, the right end of the lead 6-3 is connected to the electrode 5 at the left end of the electrically conductive layer 2-3, and the right end of the lead 6-4 is connected to the electrode 5 at the left end of the electrically conductive layer 2-4. The right end of the lead 6-5 is connected to the electrode 5 at the right end of the electrically conductive layer 2-1 and the electrode 5 at the right end of the electrically conductive layer 2-4, and the right end of the lead 6-6 is connected to the electrode 5 at the right end of the electrically conductive layer 2-2 and the electrode 5 at the right end of the electrically conductive layer 2-3. The body portion of the lead 6-5, the lead 6-1, and the lead 6-2 cover the upper surface of the upper substrate 101, and the body portion of the lead 6-6, the lead 6-3, and the lead 6-4 cover the lower surface of the lower substrate 102. Left ends of the six leads form a connector end of the strain film, for being connected to an external connector.

Embodiment 3

Figure 8:
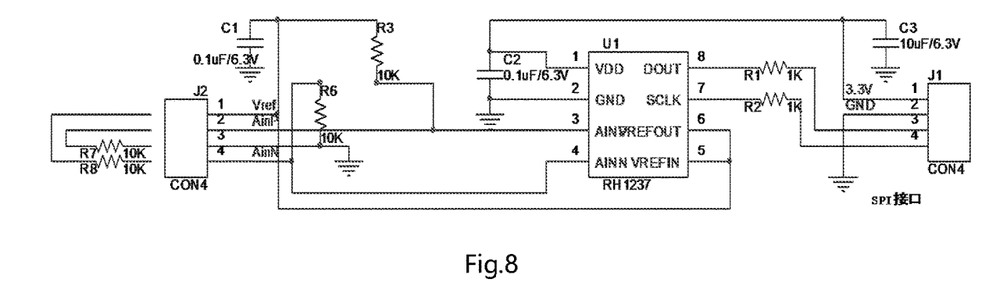
FIG. 8 is a principle diagram of a sensing circuit according to embodiment 3 of the present disclosure.
Figure 9:
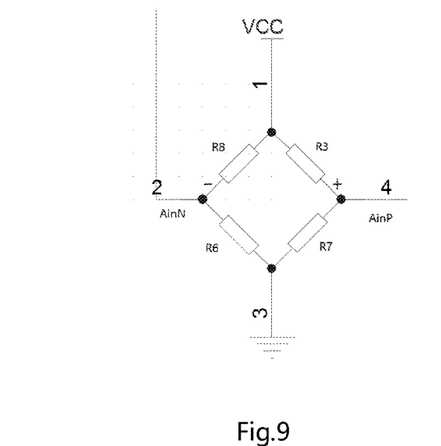
FIG. 9 is an equivalent circuit diagram of a Wheatstone bridge according to embodiment 3 of the present disclosure.

This embodiment differs from Embodiment 2 in that it is not needed to fold the flexible substrate material; two opposite bridge arms of the Wheatstone bridge cover the upper surface of the flexible substrate, and the other two resistors (e.g., SMD resistors) of the Wheatstone bridge are soldered on a PCB mainboard. A specific sensing circuit is shown in FIG. 8: R3, R6, R7, and R8 form a bridge; 2 resistors R7, R8 are disposed on the sensor, the resistance values of the two resistors R7, R8 varying with strains; R3, R6 serve as reference resistors, which are SMD resistors soldered on the PCB mainboard. The equivalent diagram is shown in FIG. 9.

Embodiment 4

Figure 10:
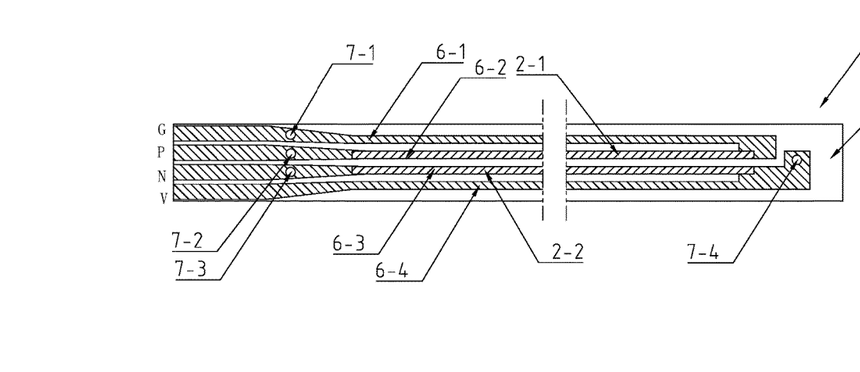
FIG. 10 is a front view of a strain film according to embodiment 4 of the present disclosure.
Figure 11:
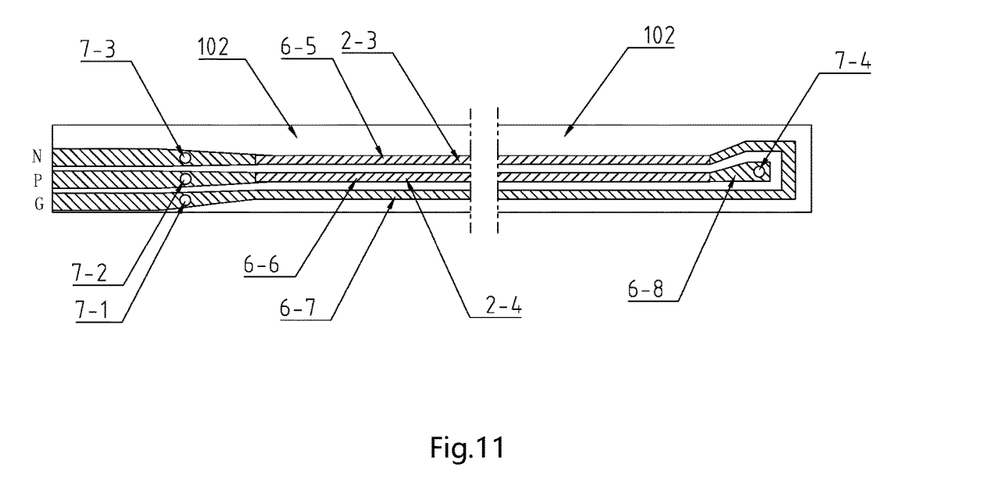
FIG. 11 is a bottom view of the strain film according to embodiment 4 of the present disclosure.

A further embodiment of a flexible sensor or electronic skin is provided, a structure of which is shown in FIG. 10 and FIG. 11, comprising eight leads, four electrically conductive layers 2, and rubber elastic layers (not shown), wherein the flexible substrate 1 is a single-layer film. The rubber elastic layers cover outside of the electrically conductive layers 2; four electrically conductive layers 2 are connected into a Wheatstone bridge; two opposite bridge arms of the Wheatstone bridge, i.e., electrically conductive layer 2-1 and electrically conductive layer 2-2, cover the upper surface 101 of the flexible substrate 1, and the other two opposite bridge arms of the Wheatstone bridge, i.e., electrically conductive layer 2-3 and electrically conductive layer 2-4, cover the lower surface 102 of the flexible substrate 1.

The leads are for example silver paste wired, and lead 6-1, lead 6-2, lead 6-3, and lead 6-4 are provided on the upper surface of the flexible substrate 1. The lead 6-1 is connected to the right end of the electrically conductive layer 2-1, and the lead 6-2 is connected to the left end of the electrically conductive layer 2-1; the lead 6-4 is connected to the right end of the electrically conductive layer 2-2; and the lead 6-3 is connected to the left end of the electrically conductive layer 2-2.

Lead 6-5, lead 6-6, lead 6-7, and lead 6-8 are provided on the lower surface of the flexible substrate 1. The lead 6-7 is connected to the right end of the electrically conductive layer 2-3, and the lead 6-5 is connected to the left end of the electrically conductive layer 2-3; the lead 6-8 is connected to the right end of the electrically conductive layer 2-4, and the lead 6-6 is connected to the left end of the electrically conductive layer 2-4.

The lead 6-1 and the lead 6-7 are electrically connected via a via-hole 7-1 and connected to Ground G at the left end; the lead 6-2 and the lead 6-6 are electrically connected via a via-hole 7-2 and connected to an output anode P at the left end; the lead 6-3 and the lead 6-5 are electrically connected via a via-hole 7-3 and connected to an output cathode N at the left end; the lead 6-4 and the lead 6-8 are electrically connected via a via-hole 7-4 and connected to the power anode V at the left end.

Embodiment 5

Figure 12:
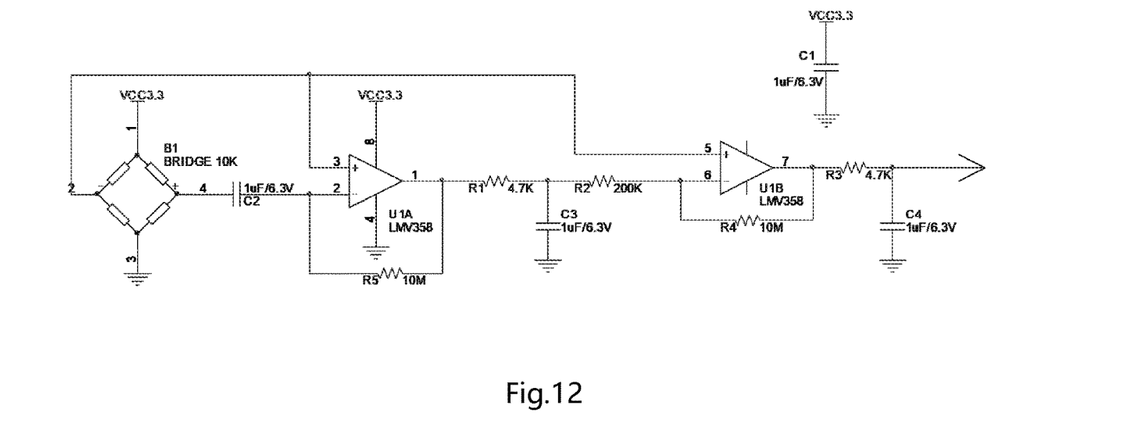
FIG. 12 is a principle diagram of a signal amplifying circuit according to embodiment 5 of the present disclosure.

The present disclosure further provides a flexible sensor sensing circuit, as shown in FIG. 12, wherein a signal amplifying circuit includes a differential capacitor, two negative feedback amplifying circuits and two low-pass filter circuits; the anode output end of a strain film B1 is connected to a first negative feedback amplifying circuit via the differential capacitor, and a first negative feedback amplifying circuit is connected to a second negative feedback amplifying circuit via a first low-pass filter circuit; and the second negative feedback amplifying circuit gives an output via a second low-pass filter circuit.

The first negative feedback amplifying circuit comprises an operational amplifier U1A and a negative feedback resistor R5, the negative feedback resistor R5 being connected to the output end and the inverting input end of the operational amplifier U1A. The second negative feedback amplifying circuit comprises an operational amplifier U1B and a negative feedback resistor R4, the negative feedback resistor R4 being connected to the output end and the inverting input end of the operational amplifier U1B.

The first low-pass filter circuit comprises a filter resistor R1 and a filter capacitor C3; the second low-pass filter circuit comprises a filter resistor R3 and a filter capacitor C4.

The anode output end of the strain film B1 is connected to the inverting input end of the operational amplifier U1A via a differential capacitor C2, and the output end of the operational amplifier U1A is connected to the inverting input end of the operational amplifier U1B via the filter resistor R1 and the negative input resistor R2, and the output end of the operational amplifier U1B gives an output via the filter resistor R3.

A first end of the filter capacitor C3 is connected to a connection point between the filter resistor R1 and the negative input resistor R2, and a second end thereof is earthed; a first end of the filter capacitor C4 is connected to an output end of the filter resistor R3, and a second end thereof is earthed.

A non-inverting input end of the operational amplifier U1A and a non-inverting input end of the operational amplifier U1B are connected to the cathode output end of the strain film B1.

When the strain film B1 is deformed, the electrically conductive layers at two faces of the strain film flexible substrate are, on one hand, stretched to increase the resistance, and on the other hand, compressed to decrease the resistance, thereby enlarging the differential value of the bridge output. The differential capacitor C2 transmits a differential signal at the instant of pressed deformation to the operational amplifier U1A; the amplified signal is low-pass filtered via R1 and C3; after the noise is removed, the amplified signal is transmitted to a second-stage amplifying circuit U1B; the amplified signal, after being low-pass filtered via R3 and C4, is outputted to an ADC to be converted into a digital signal. With this signal amplifying circuit, a very weak signal of the strain film may be amplified 10,000 times above, causing it to reach the output amplitude of the piezoelectric film.

Figure 13:
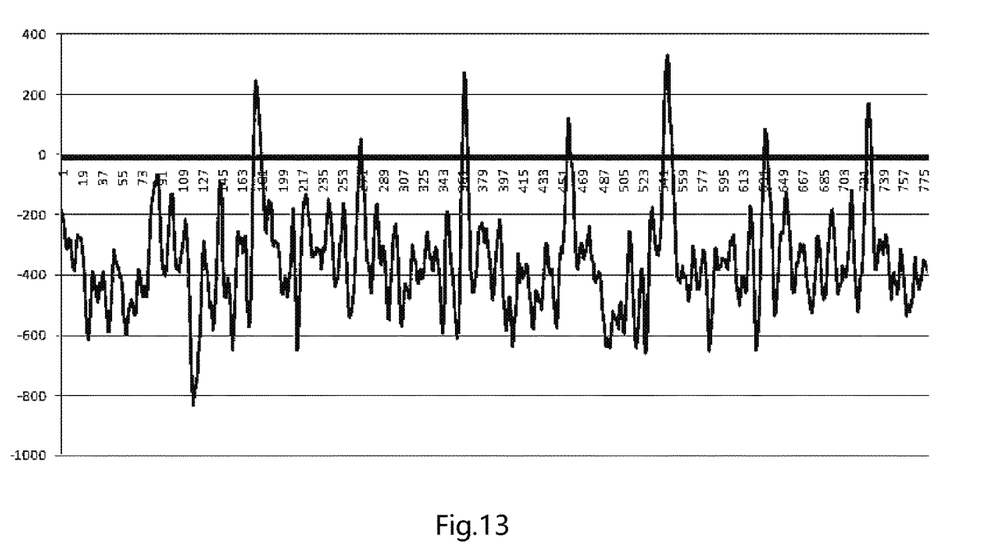
FIG. 13 is an output waveform diagram of the signal amplifying circuit according to embodiment 5 of the present disclosure.

The flexible sensor for sensing a strain according to the above embodiments of the present disclosure adopts a strain film technology, offering a simple structure, a simple processing technique, an ease of wiring, a low cost, and a high sensitivity, which may completely replace a conventional PVDF piezoelectric film. When being put on a mat, the flexible sensor for sensing a strain may sense heartbeat or breathing of a human body, wherein the measured data curve is shown in FIG. 13. When being put under a pillow, the flexible sensor for sensing a strain may also sense a heartbeat waveform. A strain film sample may be flexed into a circle with a diameter of 10 mm, which has a good flexibility and will not be damaged even after being flexed for 1 million times.

What have been described above are only preferred embodiments for implementing the present disclosure. However, the protection scope of the present disclosure is not limited thereto. Any person of normal skill in the art may easily contemplate other variations or substitutions within the technical scope of the present disclosure, all of which should be included within the protection scope of the present disclosure.

I claim:

1. A flexible sensor for sensing a strain, comprising a flexible substrate, electrically conductive layers disposed on a first surface and a second surface of the flexible substrate, and electrodes disposed at end portions of the electrically conductive layers, wherein
the electrically conductive layers include a matrix and electrically conductive particles dispersed in the matrix;
the electrically conductive particles include first electrically conductive particles and second electrically conductive particles, wherein the first electrically conductive particles include carbon powder or metal powder;
the second electrically conductive particles include carbon fibers, nanometer carbon tubes or graphene; and two ends the second electrically conductive particles face electrodes of a same direction, respectively; and
the flexible substrate includes a first flexible substrate and a second flexible substrate which are vertically folded, the first electrically conductive layer and the second electrically conductive layer cover an upper surface of the first substrate, and a third electrically conductive layer and a fourth electrically conductive layer cover a lower surface of the second substrate.

2. The flexible sensor according to claim 1, wherein: the matrix is a polymer.

3. The flexible sensor according to claim 2, wherein: the polymer is selected from the group consisting of epoxy resin, polyurethane or acrylic resin.

4. The flexible sensor according to claim 1, further comprising elastic layers, the elastic layers covering outer surfaces of the electrically conductive layers.

5. The flexible sensor according to claim 4, wherein the elastic layers are rubber layers.

6. The flexible sensor according to claim 1, wherein the flexible sensor is applied to sense heartbeat or breathing of a human body.

7. The flexible sensor according to claim 1, wherein the first electrically conductive layer is disposed over the second electrically conductive layer, and the third electrically conductive layer is disposed over the fourth electrically conductive layer, wherein the first electrically conductive layer is electrically connected to the fourth electrically conductive layer, and the second electrically conductive layer is electrically connected to the third electrically conductive layer.

8. The flexible sensor according to claim 1, further comprising leads, the leads covering a first surface and a second surface of the flexible substrate.

9. The flexible sensor according to claim 1, wherein the first flexible substrate and the second flexible substrate are integrally bonded after folding a same block of material.

10. The flexible sensor according to claim 1, wherein the electrically conductive layers form a Wheatstone bridge.

11. The flexible sensor according to claim 10, wherein a bridge resistor of the Wheatstone bridge includes an SMD resistor disposed on a PCB substrate.

12. The flexible sensor according to claim 10, further comprising a signal amplifying circuit.

13. The flexible sensor according to claim 11, wherein the signal amplifying circuit comprises a differential capacitor, a negative feedback amplifying circuit, and a low-pass filter circuit.

* * * * *